United States Patent [19]

Greco et al.

[11] Patent Number: 4,740,382

[45] Date of Patent: Apr. 26, 1988

[54] ANTIBIOTIC BONDED PROSTHESIS AND PROCESS FOR PRODUCING SAME

[75] Inventors: Ralph S. Greco, Basking Ridge; Richard Harvey, East Brunswick; Stanley Z. Trooskin, North Brunswick, all of N.J.

[73] Assignee: University of Medicine & Dentistry of New Jersey, Newark, N.J.

[21] Appl. No.: 633,615

[22] Filed: Jul. 23, 1984

[51] Int. Cl.[4] .............................. A61F 1/00; A61F 1/24
[52] U.S. Cl. .................................. 427/2; 128/334 R; 623/1; 623/12; 623/11; 623/66; 521/30
[58] Field of Search ................... 427/2; 128/334 R; 623/1, 12, 11, 66; 521/30

[56] References Cited

U.S. PATENT DOCUMENTS 3,651,043 3/1972 Schell et al. ............................ 521/30
4,442,133 4/1984 Greco et al. ............................ 427/2

*Primary Examiner*—John Kight
*Assistant Examiner*—M. L. Moore
*Attorney, Agent, or Firm*—David A. Jackson; Richard M. Goldberg; Barbara L. Renda

[57] ABSTRACT

There is disclosed an improved prosthesis coated, respectively, with a cationic surfactant, an antibiotic compound and treated with an cationic exchange compound, to remove un-antibiotic bound cationic surfactant.

27 Claims, No Drawings

ANTIBIOTIC BONDED PROSTHESIS AND PROCESS FOR PRODUCING SAME

This invention was made with Government support under Grant HL 24252 awarded by the National Institutes of Health. The Government has certain rights in this invention.

FIELD OF INVENTION

This invention relates to antibiotic bonded implants, and more particularly relates to improved antibiotic bonded surgical implants having extended antibiotic activity, reduced thrombogenicity and method for producing same.

BACKGROUND OF THE INVENTION

In an abstract presented in November 1979 to the Association for Academic Surgery, there is disclosed the bonding of oxacillin to a polytetrafluoroethylene surface coated with benzalkonium chloride for protection against infection by the device as a result of surgical implantation.

In U.S. Pat. No. 4,442,133, issued Apr. 10, 1984, there is disclosed a process for coating vascular prostheses with a cationic surfactant, such as tridodecylmethyl ammonium chloride to increase sites for antibiotic bonding, and then prior to utilization, the thus coated vascular protheses is placed in an antibiotic solution to bond the antibiotic thereto. Such antibiotic bonded vascular protheses exhibit resistance to infection.

OBJECTS OF THE INVENTION

An object of the present invention is to provide improved implantable devices having an antibiotic bonded thereto.

Yet another object of the present invention is to provide an improved implantable device having an antibiotic bonded in such a way as to substantially eliminate thrombosis of said implant.

Another object of the present invention is to provide an improved implantable device having an antibiotic bound thereto of improved release times.

SUMMARY OF THE INVENTION

These and other objects of the present invention are achieved by a prosthesis coated, respectively, with a cationic surfactant and an antibiotic, and subsequently treated with an insoluble cationic exchange compound to remove un-antibiotic bound cationic surfactant.

DETAILED DESCRIPTION OF THE INVENTION

To facilitate an understanding of the present invention, the present invention will be described with reference to the treatment of a vascular prosthesis prepared from, thermoplastic substrates, such as polytetrafluoroethylene, Dacron, polyethylene, silastic and the like, although it will be understood by one skilled in the art that the present invention relates to the treatment of any implantable device formed from such materials, e.g. catheters, heart valves, orthopedic implants, sutures, profussion pumps, etc.

In accordance with the present invention, grafts of the thermoplastic substrates, such as polytetrafluoroethylene or Dacron, are cut into 0.5 cm. segments and placed in a solution of a cationic surfactant, such as a 5% ethanol solution of tridodecylmethyl ammonium chloride (TDMAC) for a period of time of from 5 to 120 minutes, preferably about 30 minutes, at a temperature of from 0° to 55° C., preferably at ambient temperature. The grafts are air dried and thoroughly washed in distilled water to remove excess TDMAC.

The grafts having an absorbed coating of TDMAC are then placed in a solution of a negatively-charged antibiotic compound, such as penicillin, oxacillin, ticarcillin, carbenicillin, the cephalosporins or cefoxitins for a period of time of from 5 to 120 minutes, preferably 60 minutes, at a temperature of from 0° to 35° C., preferably 25° C. The thus treated grafts are then thoroughly washed, preferably in distilled water to remove unbound antibiotic material, it being understood that not all of the unbound antibiotic material is removed from the thus treated grafts.

The grafts having TDMAC/antibiotic compound bounded thereto are immersed in a slurry of a particulate insoluble cationic exchange compound, such as Sepharose-CM, cross-linked agarose having carboxyl methyl groups ($CH_2$—COO—) attached thereto for a period of time of from 6 to 72 hours, preferably 20 hours, at a temperature of from 0° to 35° C., preferably 25° C. The cationic exchange compound is in the form of beads having a particle size distribution of from 5 to 40 microns and is commercially available in such particle size distribution. The thus treated grafts are then thoroughly washed in distilled water.

Implantable devices or prosthesis treated in accordance with the present invention improve the molar ratio of antibiotic compound bounding per TDMAC molecule of up to 0.5, i.e. one molecule of antibiotic compound to two molecules of cationic surfactant, as compared with the molar ratio of 0.25, i.e. a one-hundred percent (100%) increase, as compared by the process of the hereinabove discussed U.S. Letters Patent.

While Applicant does not wish to be bound by any theory of invention, it appears that the cationic exchange compound has a high affinity for bound TDMAC molecules which are not shielded by a bound antibiotic molecule, and thus reduce any thrombosis effect by the TDMAC. Further, the surface of the prosthesis, at a microscope level, are filamentous with ridges and deep recesses. The molecules of TDMAC and antibiotic compound are relatively small and presumably bind uniformly on the exposed ridges and the interstices of the prosthesis surface.

The particles of the cationic exchange compound, such as the Sepharose-CM, is sterically unable to penetrate into the deep valleys and surfaces of the prosthesis. Thus, the TDMAC and antibiotic molecules remain bonded in such recesses for a longer period of time. It has preliminarily been found that the amount of antibiotic compound remaining after exposure to plasma is more slowly released ($t_{\frac{1}{2}}=12$ hours) as composed with a prosthesis not treated with an cationic exchange compound ($t_{\frac{1}{2}}=2$ hours). Thus, the present invention yields a surface which is less thrombogenic, yet containing a sequestered reservoir of an antibiotic compound, and exhibiting a reduced tendency to cause blood platelet aggregation.

As hereinabove discussed, the beads of immobilizing cationic surfactant (commercially available) are of a particle size distribution of from 5 to 40 microns. It is believed that still further improved results would be obtained if the particle size distribution of the beads was more closely that of the diameter of the blood platelets, i.e. about 2 microns. Thus, the beads of such a size of the cationic exchange compound would be permitted to move more closely into the recess of a treated device to remove more of the un-antibiotic bound TDMAC molecules.

In addition to the Sepharose-CM, effective cationic exchange compounds include Sulphopropylcellulose (SP-Sephadex), etc.

Numerous modifications and variations of the present invention are possible in light of the above teachings and, therefore, within the scope of the appended claims, the invention may be practiced otherwise than as particularly described.

What is claimed is:

1. A prosthesis for use in in vivo surgery having a coating, respectively, of a cationic surfactant and an antibiotic compound offering a charge opposite to that of said surfactant and bound to said surfactant, wherein said coating is discontinuous as to areas where said cationic surfactant lacks antibiotic bound thereto, said cationic surfactant having been removed in said areas the application thereto and removal of an immobilizing cationic exchange compound.

2. The prosthesis as defined in claim 1 wherein said antibiotic compound is selected from the group consisting of penicillin, oxacillin, ticarcillin, carbenicillin, a cephalosporin and a cefoxitin.

3. The prosthesis as defined in claim 1 wherein said cationic surfactant is tridodecylmethyl ammonium chloride.

4. The prosthesis as defined in claim 1 wherein said cationic exchange compound is Sheparose-CM.

5. The prosthesis as defined in claim 1 wherein said prosthesis is a vascular graft.

6. A method for preparing a prosthesis for use in in vivo surgery, which comprises:
    (a) contacting said prosthesis with a cationic surfactant to coat said prosthesis with said cationic surfactant;
    (b) contacting said prosthesis of step (a) with a solution of an antibiotic compound offering a charge opposite to that of said surfactant; and
    (c) contacting said prosthesis of step (b) with an cationic exchange compound to remove cationic surfactant not bound to said antibiotic compound.

7. The method as defined in claim 6 wherein the prosthesis of step (a) is washed to remove excess cationic surfactant prior to step (b).

8. The method as defined in claims 6 or 7 wherein said prosthesis of step (b) is washed to remove unbound antibiotic compound prior to step (c).

9. The method as defined in claim 6 wherein step (a) is effected for a period of time of from 5 to 120 minutes.

10. The method as defined in claim 9 wherein step (a) is effected preferably for a period of 30 minutes.

11. The method as defined in claim 6 wherein step (a) is effected at a temperature of from 0° to 55° C.

12. The method as defined in claim 11 wherein step (a) is effected preferably at ambient temperature.

13. The method as defined in claim 6 wherein step (b) is effected for a period of time of from 5 to 120 minutes.

14. The method as defined in claim 13 wherein step (b) is effected preferably for about 30 minutes.

15. The method as defined in claim 6 wherein step (b) is effected at a temperature of from 0° to 35° C.

16. The method as defined in claim 15 wherein step (b) is effected preferably at a temperature of 25° C.

17. The method as defined in claim 6 wherein step (c) is effected for a period of time of from 6 to 72 hours.

18. The method as defined in claim 17 wherein step (c) is effected preferably for a period of time of 20 hours.

19. The method as defined in claim 6 wherein step (c) is effected at a temperature of from 0° to 35° C.

20. The method as defined in claim 19 wherein the step (c) is effected preferably at a temperature of 25° C.

21. The method as defined in claim 6 wherein said cationic exchange compound is particulate.

22. The method as defined in claim 21 wherein said particulate cationic surfactant has a particle size range of from 2 to 40 microns.

23. The method as defined in claim 22 wherein said particle size is about 2 microns.

24. The method as defined in claim 6 wherein said cationic surfactant is tridodecylmethyl ammonium chloride.

25. The method as defined in claim 6 wherein said antibiotic compound is selected from the group consisting of penicillin, oxacillin, ticarcillin, carbenicillin, a cephalosporin and a cefoxitin.

26. The method as defined in claim 6 wherein said cationic exchange compound is selected from the group consisting of Sepharose-CM and SP-Sephadex.

27. The method as defined in claim 26 wherein said cationic exchange compound is Sepharose-CM.

* * * * *